US010058716B2

(12) United States Patent
Ma et al.

(10) Patent No.: US 10,058,716 B2
(45) Date of Patent: Aug. 28, 2018

(54) MICRO-EMULSIFIER FOR ARTERIAL THROMBUS REMOVAL

(75) Inventors: Jan Ma, Singapore (SG); Adrian Fatt Hoe Low, Singapore (SG); Yin Chiang Boey, Singapore (SG)

(73) Assignee: Nanyang Technological University, Singapore (SG)

( * ) Notice: Subject to any disclaimer, the term of this patent is extended or adjusted under 35 U.S.C. 154(b) by 523 days.

(21) Appl. No.: 12/231,631

(22) Filed: Sep. 3, 2008

(65) Prior Publication Data
US 2010/0057097 A1    Mar. 4, 2010

(51) Int. Cl.
A61B 17/32    (2006.01)
A61N 7/00    (2006.01)
A61B 17/22    (2006.01)

(52) U.S. Cl.
CPC .......... *A61N 7/00* (2013.01); *A61B 17/22004* (2013.01); *A61N 2007/0039* (2013.01); *A61N 2007/0043* (2013.01)

(58) Field of Classification Search
CPC .............................................. A61B 17/22004
USPC ....... 606/127, 128, 159, 161, 166, 167, 169, 606/170; 601/4; 604/22, 27, 542
See application file for complete search history.

(56) References Cited

U.S. PATENT DOCUMENTS 3,433,226 A * 3/1969 Boyd ............... A61B 17/22012
601/4
4,750,902 A   6/1988 Wuchinich et al.
4,979,952 A * 12/1990 Kubota ............ A61B 17/22012
310/316.01
5,069,664 A * 12/1991 Guess et al. .................... 604/22
5,419,761 A   5/1995 Narayanan et al.
5,725,494 A * 3/1998 Brisken ........................... 604/22
6,283,974 B1  9/2001 Alexander
6,887,252 B1 * 5/2005 Okada et al. ................. 606/169
7,374,551 B2  5/2008 Liang et al.
2003/0036705 A1  2/2003 Hare et al.
(Continued)

FOREIGN PATENT DOCUMENTS

WO    WO 93/13715        7/1993
WO    WO 1995/01751 A1   1/1995
(Continued)

OTHER PUBLICATIONS

First Office Action for corresponding Chinese application No. 200880131810.3, Jan. 11, 2013, 8 pages.
(Continued)

*Primary Examiner* — Gregory Anderson
*Assistant Examiner* — Sarah Simpson
(74) *Attorney, Agent, or Firm* — Womble Bond Dickinson (US) LLP

(57) ABSTRACT

Disclosed is a micro-emulsifier comprising a stack of piezoelectric materials, a horn at a proximal end of the stack of piezoelectric materials, and a transmission wire receivable in the horn for transmission of ultrasound waves able to be produced by the stack of piezoelectric materials. The ultrasound waves are able to be produced in a direction parallel to a longitudinal axis of the stack of piezoelectric materials and the horn. The transmission wire comprises a first end receivable in the horn and a second end remote from the first end, the second end having a bulb thereon.

18 Claims, 2 Drawing Sheets

(56) References Cited

U.S. PATENT DOCUMENTS

| | | | |
|---|---|---|---|
| 2003/0225332 A1* | 12/2003 | Okada | A61B 17/320068 600/439 |
| 2004/0082884 A1* | 4/2004 | Pal et al. | 601/2 |
| 2004/0162546 A1 | 8/2004 | Liang et al. | |
| 2004/0162571 A1 | 8/2004 | Rabiner et al. | |
| 2005/0215942 A1* | 9/2005 | Abrahamson et al. | 604/22 |
| 2007/0066978 A1 | 3/2007 | Schafer et al. | |
| 2008/0039746 A1 | 2/2008 | Hissong et al. | |

FOREIGN PATENT DOCUMENTS

| | | |
|---|---|---|
| WO | WO 00/00096 | 1/2000 |
| WO | WO 2007/030422 A2 | 3/2007 |

OTHER PUBLICATIONS

Second Office Action for corresponding Chinese application No. 200880131810.3, Aug. 8, 2013, 7 pages.

Third Office Action for corresponding Chinese application No. 200880131810.3, Feb. 27, 2014, 6 pages.

* cited by examiner

MICRO-EMULSIFIER FOR ARTERIAL THROMBUS REMOVAL

FIELD

This invention relates to a micro-emulsifier for arterial thrombus removal and refers particularly, though not exclusively, to the ultrasound ablation of thrombus by miniaturized piezoelectric transducer with a flexible transmission wire and to emulsification of biological matter such as the phacoemulsification of the thrombi.

BACKGROUND

A thrombus is a blood clot that forms in a blood vessel and remains there. This can result in damage, destruction (infarction), or even death of the tissue (necrosis) in that area. Thrombus surgery is a common procedure. There have been many different surgical tools developed for thrombus removal. These include tools that remove the thrombus by mechanical force, use of thrombolytic agents, and ultrasonic energy. However, these techniques suffer from a number of drawbacks including, but not limited to, low efficiency and damage to blood vessel wall.

Piezoelectric devices for thrombolytic ablation have been developed. The actuator has an external power generator that supplies the actuator with the electrical energy required to produce ultrasonic energy. A transducer of lead zirconate titanate ("PZT") crystals converts the electrical energy to high-power ultrasonic waves. An ultrasound catheter, connected at the proximal end of the transducer, transmits the ultrasonic waves to the target thrombus at its distal end. The ablation of the thrombus by ultrasound is by cavitation in the blood clot caused by the ultrasonic waves.

Ultrasonic tissue ablation exhibits tissue selectivity. The susceptibility of biological tissues to ultrasonic disruption is inversely proportional to their elastic recoil, which represented by their collagen and elastin content. While thrombi are poorly endowed with elastic elements, they are highly susceptible to ultrasonic ablation. Conversely, the normal arterial wall, which is rich with compliant matrix of collagen and elastin, is relatively spared. Since cavitation is bioselective, aortic walls are resistant to cavitation leaving only the thrombus ablated by the actuator described above.

One example of an ultrasonic catheter used to treat human blood vessels delivers solutions containing dissolution compounds directly to the occlusion site to remove or reduce the occlusion. In addition, ultrasonic energy is generated by an ultrasound assembly and is used to enhance the therapeutic effect of the dissolution compounds. Since only the catheter is inserted into the blood vessel and the transducer is outside the body, the input power needed will be high to provide sufficient ultrasound energy to the catheter for thrombolysis. Also, due to the long length of the catheter energy loss along the catheter will be high. This means that efficiency will decrease due to the energy loss.

Another example uses a transcranial ultrasound thrombolysis system that uses ultrasonic energy in combination with thrombolytic agents to assist in dissolving intracranial thrombi and to enhance the efficacy of the thrombolytic agents. However, the large dimensions of the system have limited its practical application.

A further example of an ultrasonic medical device is used to treat deep vein thrombosis by using ultrasonic energy with plurality of transverse node and anti-nodes along the longitudinal axis of the ultrasonic probe to generate cavitation to ablate the thrombus and treat deep vein thrombosis. The transverse ultrasonic vibration may damage surrounding cells instead of just the thrombus. Also, it is less localized to the thrombus as only a catheter is inserted into the body.

The prior art does not provide a suitable device to be inserted into body that is able to ablate, emulsify and remove the thrombus. The prior art does not provide a solution to better localize to the thrombus site to have higher precision as is required in human applications. The prior art uses high input power to generate low frequency ultrasound energy. They suffer from large energy losses during the conversion. Thus, there remains a need for a device that is small in size so that can be inserted into body and is able to ablate, emulsify and remove thrombus. This is preferably in a more localized manner.

SUMMARY

According to a first exemplary aspect there is provided a micro-emulsifier comprising a stack of piezoelectric materials, a horn at a proximal end of the stack of piezoelectric materials, and a transmission wire receivable in the horn for transmission of ultrasound waves able to be produced by the stack of piezoelectric materials. The ultrasound waves are able to be produced in a direction parallel to a longitudinal axis of the stack of piezoelectric materials and the horn.

According to another exemplary aspect there is provided a micro-emulsifier comprising a stack of piezoelectric materials, a horn at a proximal end of the stack of piezoelectric materials, and a transmission wire receivable in the horn for transmission of ultrasound waves able to be produced by the stack of piezoelectric materials. The transmission wire comprises a first end receivable in the horn and a second end remote from the first end, the second end having a bulb thereon.

For the first exemplary aspect, the transmission wire may comprise a first end receivable in the horn and a second end remote from the first end, the second end having a bulb thereon.

According to a further exemplary aspect there is provided a transmission wire for a micro-emulsifier, the transmission wire comprising a first end configured to be receivable in a horn of the micro-emulsifier, and a second end remote from the first end, the second end having a bulb thereon.

For all three exemplary aspects, the bulb may be at least one of: integral with the second end, and secured to the second end. The bulb may have a smooth outer surface. The outer surface may be irregular or a ball. The transmission wire may be flexible; and may be of a metal material.

For the first two exemplary aspects the ultrasound waves may be able to be produced in a direction parallel to a longitudinal axis of the stack of piezoelectric materials and the horn. The stack of piezoelectric materials may comprise a plurality of piezoelectric elements. Each piezoelectric element may comprise a cylinder with a hollow core. Each piezoelectric element may cyclically compress and expand in the direction parallel to a longitudinal axis of the stack of piezoelectric materials and the horn. The horn may be a hollow tube and may receive therein the transmission wire for transmission of longitudinal ultrasound waves. The transmission wire may be received in a manner of a force fit or a snap fit. The junction of the transmission wire and the horn may use a securing agent and/or a sealing agent. Alternatively, the transmission wire may be integral with the horn.

The micro-emulsifier may be able to be accommodated in a major blood vessel, and the transmission wire may be able to be located in a small blood vessel for ablation of a thrombus in the small blood vessel.

According to a final exemplary aspect there is provided a method of ablating a thrombus in a first blood vessel, the method comprising: passing a micro-emulsifier as described above along a large blood vessel able to accommodate the micro-emulsifier until the transmission wire contacts the thrombus in the larger blood vessel, or enters a smaller blood vessel and contacts a thrombus in the smaller blood vessel, actuating the micro-emulsifier to creating longitudinally-directed ultrasonic energy at the bulb to ablate the thrombus. The ablation of the thrombus may be by at least one of cavitation and mechanical fragmentation. Ablation may include emulsification, defragmentation and thromblysis.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings.

In the drawings.

DETAILED DESCRIPTION

Figure 1:
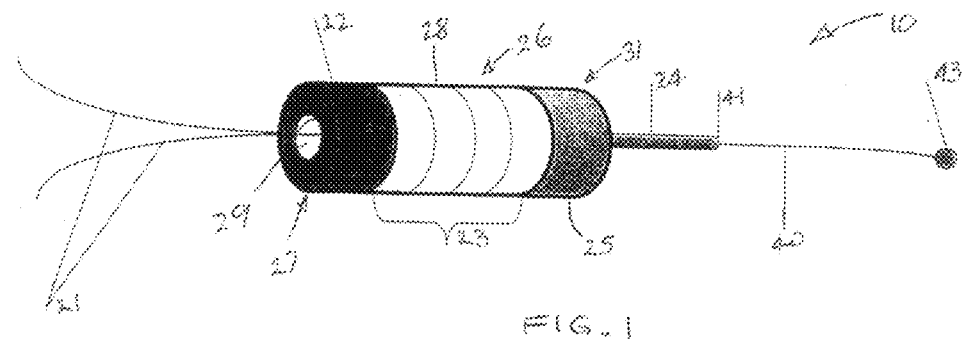
FIG. 1 is a schematic diagram of an exemplary embodiment of a micro-emulsifier.
Figure 2:
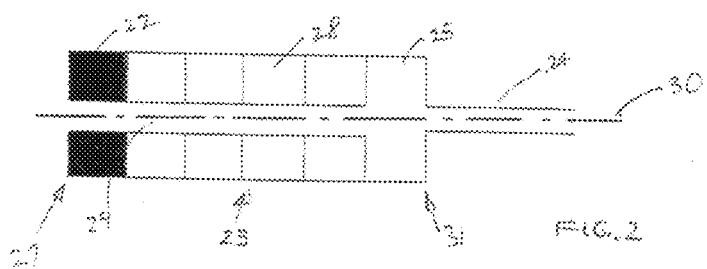
FIG. 2 is a longitudinal vertical cross-sectional view of the transducer of the exemplary embodiment of FIG. 1.
Figure 3:
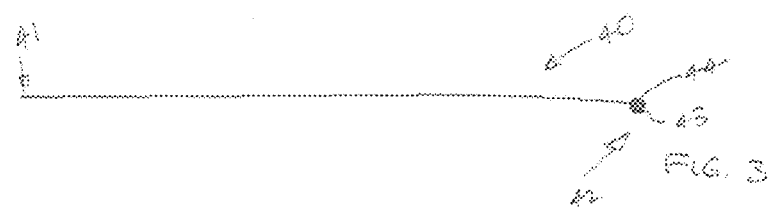
FIG. 3 is a schematic view of the transmission wire of the exemplary embodiment of FIGS. 1 and 2.

Shown in FIGS. 1 to 3 is a micro-emulsifier 10 comprising a transducer 20 and a transmission wire 40.

The transducer 20 converts electrical energy to high-power ultrasonic energy and comprises a pair of electrical leads 21 for the supply of electrical energy to the transducer 20. Alternatively, in-built or removable batteries may be provided in the transducer 20. Further alternatively, radio frequency waves may be used for supply of energy via an inbuilt antenna (not shown) in the transducer 20. As shown, the leads 21 are connected to a body 26 of the transducer 20 at the remote end 27 of the transducer 20.

Figure 4:
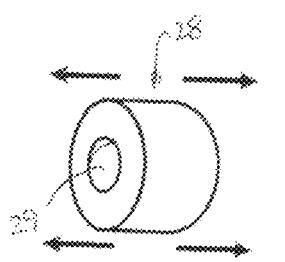
FIG. 4 is a schematic view illustrating the contraction and expansion of the piezoelectric material for the exemplary embodiment of FIGS. 1 and 2.
Figure 4:
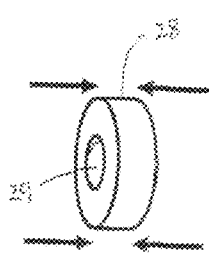

The body 26 of the transducer 20 further comprises actuating coils 22 and a stack 23 of piezoelectric materials 28. Each of the piezoelectric materials 28 of the stack 23 may be of lead zirconate titanate ("PZT") crystals. As shown in FIG. 4, each of the piezoelectric materials 28 of the stack 23 is preferably cylindrical with a hollow core 29. Each piezoelectric material 28 contracts and expands in the direction of the central longitudinal axis 30 of the transducer 20. By having a stack 23 of piezoelectric materials 28 a multi-layer amplification is promoted such that the piezoelectric stack 23 acts as an amplifier. Although a stack 23 is described and illustrated, a single ring 28 or a tube (a long ring) may be used. This may be of assistance where the micro-emulsifier 10 is to be further miniaturized.

The diameter of piezoelectric stack 23 may be, for example, 5 mm and the length may be, for example, 8 mm. In this way the micro-emulsifier 10 is able to be placed within a major blood vessel.

At its proximal end 31 the body 26 of the transducer 20 has a horn 24 of known form and construction such as a hollow tube, as shown. The horn 24 transmits and amplifies the ultrasonic energy to the transmission wire 40 and is mounted to the body 26 by means of a horn base 25. The horn 24 is a hollow tube and is for receiving therein the transmission wire 40. The diameter of horn 24 may be, for example, 1.5 mm and its length may be, for example in the range 20 to 30 mm.

The horn 24 may be of any suitable material such as, for example, 7075 aluminum material. Aluminum has a low density which assists in the amplification of the ultrasonic waves produced by the transducer 20. It also means the mass of piezoelectric stack 23 is relatively larger than the mass of the horn 24.

If the piezoelectric stack 23 has a mass of $m_1$ and will generate a velocity of $v_1$ and the horn has a mass of $m_2$ and will generate a velocity of $v_2$ then, due to the conservation of energy, $$m_1 v_1 = m_2 v_2$$

As $m_1$ is larger than $m_2$ therefore $v_2$ will be larger than $v_1$. This promotes an amplifying effect. Since the amplitude generated by the piezoelectric stack 23 is not large due to its dimension and physical properties, the horn 24 will act as an amplifier of the ultrasonic waves produced by the piezoelectric stack 23.

The transmission wire 40 has a first end 41 for mounting within the horn 24 and a second end 42 having thereon a bulbous portion 43. The transmission wire 40 transmits the ultrasonic energy to the target thrombus at the second end 42. The transmission wire 40 has the ultrasound waves focused at the bulbous portion 43.

The transmission wire 40 is connected at the proximal end of the horn 24 and may be of a diameter in the range 0.3 to 0.7 mm, preferably 0.5 mm. The length of the transmission wire 40 may be in the range 10 to 40 cm, preferably 15 cm. The shorter is the length of the transmission wire 40, the less is the energy loss and the better the efficiency. The length of the transmission wire 40 is determined by the wavelength of the frequency that is generated by the transducer 20 ($n*\frac{1}{2}\lambda$, where n is integer).

The second end 42 of the transmission wire 40 has the bulb 43 which preferably has a smooth shape and may approximate a ball. It may be integral with the transmission wire 40, or may be securely attached to the transmission wire 40. It may be of, for example, a polymer such as an epoxy and may have a diameter in the range 1.0 to 2.0 mm, preferably 1.5 mm. This enables the transmission wire to extend from the transducer 20 into small blood vessels such as, for example, coronary arteries. As such the transducer 20 may remain in a blood vessel of larger diameter and that is able to accommodate it, and the transmission wire 40 can extend into smaller diameter blood vessels for the phacoemulsification of the thrombus.

The bulb 43 is that part of the micro-emulsifier 10 that contacts the thrombus. A uniform and smooth surface 44 is preferred. The ball shape illustrated may increase the contact area with the thrombus. The smooth surface 44 assists in preventing damage to the wall of the blood vessels during insertion and/or operation. The surface 44 may be non-uniform to increase the friction of the surface 44 to enhance the phacoemulsification of the thrombus. The transmission wire is preferably flexible so it can follow the path of the blood vessels to reach the site of the thrombus.

The transmission wire 40 is preferably of a material that has a crystalline structure suitable for the transmission of ultrasound waves. As such it is preferably a metal, more preferably a hard metal. It is also preferably flexible. As ultrasound energy is best transmitted in or by a solid metal, the transmission wire 40 is preferably of, for example, stainless steel or titanium. As the micro-emulsifier 10 is inserted into a body, the material must be suitable for that purpose. Titanium, Ti-6Al-4V (Grade 5) been used with excellent biocompatibility and high fatigue strength at 1E+7 cycles with $K_t=3.3$. It also has high flexibility so that it can bend and change shape when inserted into a blood vessel.

The connection of the transmission wire 40 with the horn 24 may be by insertion of the transmission wire 40 into the horn 24 in the manner of a force fit or a snap fit and/or may use a securing and/or sealing agent such as, for example, an epoxy, welding, or the like. The connection should be such as to minimize the loss of ultrasound energy in transmission from the horn 24 to the transmission wire 40. A good seal between the transmission wire 40 and the horn 24 will assist in this regard. Alternatively, the transmission wire 40 may be integral with the horn 24.

Figure 5:
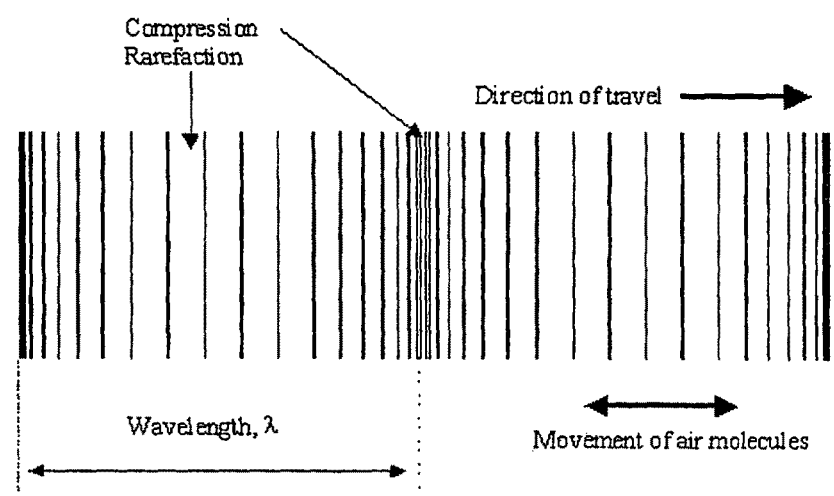
FIG. 5 is an illustration of the longitudinal wave pattern produced by the operation of the exemplary embodiment of FIGS. 1 to 4.

The cylindrical nature of the piezoelectric elements 28 of the stack 23 induces sequential contraction and expansion of the piezoelectric elements 28 to produce a longitudinally-directed ultrasound wave as shown in FIG. 5. The ultrasound waves may have a frequency in the range of, for example, 20 to 100 KHz, preferably 60 KHz.

There is a combination of two synergistic mechanisms involved in ablation of a thrombus by the micro-emulsifier 10. The first mechanism is a cavitation effect. During the negative phase of the acoustic cycle, the pressure falls below the vapor pressure of the thrombus. As such the high ultrasound energy applied may cause the formation of micro-bubbles or cavities in the thrombus. Local shock waves may be generated by rapid expansion and collapse of the cavities. Relatively violent implosion of the micro-bubbles or cavities may lead to tissue disruption. The role of cavitation in the ablation effect of ultrasound is corroborated by the finding that tissue ablation is observed only at powers above the cavitation threshold.

Mechanical fragmentation of the target thrombus is the second mechanism. This is caused by the high-frequency, low-amplitude longitudinal displacement of the bulb 44 of the transmission wire 40 due to the ultrasound waves. However, additional lateral motion of the transmission wire 40, or an additional cavitation effect, may occur at the same time.

Since thrombi appear to be more susceptible to ultrasonic disruption, it is suggested that cavitation is the principal mechanism of thrombus ablation. It leads to depolymerization of fibrin polymers, thus causing thrombus fragmentation.

All of the micro-emulsifier 10 can be inserted into a blood vessel instead of only the catheter or transmission wire as with the prior art. This increases efficiency. The length, strength and flexibility of the transmission wire 40, together with the bulb 44, enable the micro-emulsifier to be passed along larger blood vessels able to accommodate it until the transmission wire contacts the thrombus in the larger blood vessel, or enters a smaller blood vessel and contacts a thrombus in the smaller blood vessel. The longitudinal nature of the ultrasonic waves rather than lateral sound waves can ablate the thrombus with minimal risk of damage to the wall of the small blood vessel. This may be with lower input power and higher efficiency.

The micro-emulsifier 10 may be placed at a tip of a standard vacuum catheter allowing a smooth delivery towards the thrombus site. At the vicinity of the thrombus, the micro-emulsifier 10 will be actuated, creating longitudinally-directed ultrasonic energy at the bulb 44, which will ablate the thrombus. The device generates ultrasonic energy locally and hence higher precision in human application. These will naturally simplify the procedure and reduce side effects.

The ablation of the thrombus is to be taken as including emulsification, defragmentation, thromblysis, and so forth. It may take place by two different actions:
(a) mechanical impact. Here the vibration of the bulb 44 will smash the thrombus. In this effect, even without wave propagation the thrombus can be destroyed. For this reason the transmission wire 40 should not be of a great length.
(b) cavitation: Here the ultrasonic energy propagate in the thrombus as pressure
and/or stress waves that destroy the thrombus by ablation, emulsification, defragmentation, thromblysis, and so forth.

The micro-emulsifier 10 may be used for, for example:
lysis of clots in the aorta and its branch arteries;
lysis of clots in the coronary arteries;
lysis of clots in the venous system;
improvement of blood flow within the myocardium;
lysis of clots in the cerebral vasculature; and
lysis of clots in the pulmonary arteries.

Whilst the foregoing description has described exemplary embodiments, it will be understood by those skilled in the technology concerned that many variations in details of design, construction and/or operation may be made without departing from the present invention.

What is claimed is:

1. A micro-emulsifier including a transducer, the micro-emulsifier comprising:
    actuating coils;
    only one piezoelectric element comprising a cylinder with a hollow core, the piezoelectric element configured to contract and expand in the longitudinal axis of the transducer;
    a horn at a proximal end of the piezoelectric element, the horn including a hollow tube that extends the entire length of the horn; and
    a flexible transmission wire of solid metal for transmission of ultrasound waves able to be produced by the piezoelectric element, the ultrasound waves being able to be produced in a direction parallel to a longitudinal axis of the piezoelectric element and the horn, wherein the micro-emulsifier is configured for insertion of all of the micro-emulsifier into a human blood vessel for generating ultrasonic energy locally at a vicinity of a thrombus to ablate the thrombus, wherein the horn transmits and amplifies the ultrasonic energy, and wherein the transmission wire is integral with the horn.

2. The micro-emulsifier as claimed in claim 1, wherein the transmission wire comprises:
    a first end integral with the horn and
    a second end remote from the first end, the second end having a bulb thereon.

3. The micro-emulsifier as claimed in claim 2, wherein the bulb has a smooth outer surface.

4. The micro-emulsifier as claimed in claim 3, wherein the outer surface is of a shape selected from the group consisting of: irregular, and ball.

5. The micro-emulsifier as claimed in claim 2, wherein the bulb is at least one of: integral with the second end, and securely attached to the second end.

6. The micro-emulsifier as claimed in claim 1, wherein the piezoelectric element cyclically compresses and expands in the direction parallel to a longitudinal axis of the piezoelectric element and the horn.

7. The micro-emulsifier as claimed in claim 1, wherein the micro-emulsifier is able to be accommodated in a major blood vessel, and the transmission wire is able to be located in a small blood vessel for ablation of a thrombus in the small blood vessel.

8. The micro-emulsifier as claimed in claim 1, wherein the piezoelectric element has a diameter of 5 mm and a length of 8 mm.

9. A micro-emulsifier including a transducer, the micro-emulsifier comprising:
   actuating coils;
   only one piezoelectric element comprising a cylinder with a hollow core, the piezoelectric element configured to contract and expand in the longitudinal axis of the transducer;
   a horn at a proximal end of the piezoelectric element, the horn including a hollow tube that extends the entire length of the horn; and
   a flexible transmission wire of solid metal for transmission of ultrasound waves able to be produced by the piezoelectric element, the transmission wire comprising a first end integral with the horn and a second end remote from the first end, the second end having a bulb thereon, wherein the micro-emulsifier is configured for insertion of all of the micro-emulsifier into a human blood vessel for generating ultrasonic energy locally at a vicinity of a thrombus to ablate the thrombus, wherein the horn transmits and amplifies the ultrasonic energy, and wherein the transmission wire is integral with the horn.

10. The micro-emulsifier as claimed in claim 9, wherein the bulb is at least one of: integral with the second end, and secured to the second end.

11. The micro-emulsifier as claimed in claim 9, wherein the ultrasound waves are able to be produced in a direction parallel to a longitudinal axis of the piezoelectric materials and the horn.

12. The micro-emulsifier as claimed in claim 9, wherein the bulb has a smooth outer surface.

13. The micro-emulsifier as claimed in claim 12, wherein the outer surface is of a shape selected from the group consisting of: irregular, and ball.

14. The micro-emulsifier as claimed in claim 9, wherein the piezoelectric element cyclically compresses and expands in the direction parallel to a longitudinal axis of the piezoelectric element and the horn.

15. The micro-emulsifier as claimed in claim 9, wherein the micro-emulsifier is able to be accommodated in a major blood vessel, and the transmission wire is able to be located in a small blood vessel for ablation of a thrombus in the small blood vessel.

16. A method of ablating a thrombus in a human blood vessel using a micro-emulsifier including a transducer, the method comprising:
   passing a micro-emulsifier comprising actuating coils, only one piezoelectric element comprising a cylinder with a hollow core, the piezoelectric element configured to contract and expand along the longitudinal axis of the transducer, a horn at a proximal end of the piezoelectric element, the horn including a hollow tube that extends the entire length of the horn, and a flexible transmission wire of solid metal for transmission of ultrasound waves able to be produced by the piezoelectric element along a larger human blood vessel able to accommodate all of the micro-emulsifier in the larger human blood vessel until the transmission wire contacts the thrombus in the larger human blood vessel, or the transmission wire enters a smaller human blood vessel and contacts a thrombus in the smaller human blood vessel, wherein the transmission wire comprises a first end integral with the horn and a second end remote from the first end, the second end having a bulb thereon, wherein the transmission wire is integral with the horn, and wherein the horn transmits and amplifies the ultrasonic energy,
   actuating the micro-emulsifier at the vicinity of the thrombus to create longitudinally-directed ultrasonic energy at the bulb to ablate the thrombus.

17. The method as claimed in claim 16, wherein the ablation of the thrombus is by at least one of cavitation and mechanical fragmentation.

18. The method as claimed in claim 16, wherein ablation includes emulsification, defragmentation and thromblysis.

* * * * *